United States Patent [19]

Glamkowski et al.

[11] Patent Number: 4,971,992
[45] Date of Patent: Nov. 20, 1990

[54] CARBONATE DERIVATIVES OF ESEROLINE

[75] Inventors: Edward J. Glamkowski, Warren; Yulin Chiang, Convent Station; Barbara E. Kurys, Morris Plains, all of N.J.

[73] Assignee: Hoechst-Roussel Pharmaceuticals Inc., Somerville, N.J.

[21] Appl. No.: 329,171

[22] Filed: Mar. 27, 1989

[51] Int. Cl.$^5$ ............... C07D 487/04; A61K 31/40
[52] U.S. Cl. ................................ 514/411; 548/429
[58] Field of Search .................... 514/411; 548/429

[56] References Cited

U.S. PATENT DOCUMENTS 4,791,107 12/1988 Hamer ........................ 548/429

OTHER PUBLICATIONS

Harris et al., J. Pharm. Exp. Ther. 169, 17 (1969).
Furst, Eur. J. Pharmacol. 83, 233 (1982).
Pearl, J. Pharmacol. Exp. Ther. 160, 217 (1968).
Dewey, J. Pharm. Pharmacol. 21, 548 (1969).

Primary Examiner—Mark L. Berch
Attorney, Agent, or Firm—Jerome Rosenstock

[57] ABSTRACT

This invention relates to 1,2,3,3a,8,8a-hexahydro-1,3a,8-trimethylpyrrolo[2,3-b]indol-5-ol carbonate esters of the

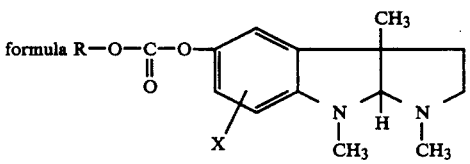

where R is lower alkyl, cycloalkyl, aryl, aralkyl and

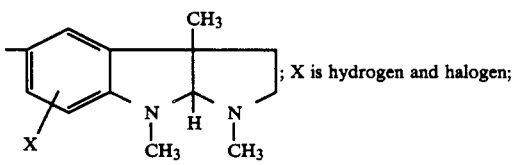

; X is hydrogen and halogen;

the pharmaceutically acceptable acid addition salts thereof and where applicable to the geometric and optical isomers and racemic mixtures thereof. The compounds of this invention display utility as analgesic agents.

24 Claims, No Drawings

CARBONATE DERIVATIVES OF ESEROLINE

This invention relates to compounds of the formula

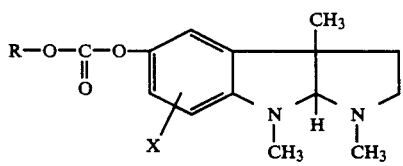

where R is loweralkyl, cycloalkyl, aryl, aralkyl and 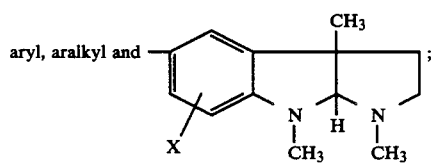;

X is hydrogen and halogen.

Throughout the specification and appended claims, a given chemical formula or name shall encompass all geometric and optical isomers thereof and racemic mixtures where such isomers and mixtures exist.

In the above definitions, the term "lower" means the groups it is describing contain from 1 to 8 carbon atoms. The term "alkyl" refers to a straight or branched chain hydrocarbon containing no unsaturation, e.g. methyl, ethyl, isopropyl, 2-butyl, neopentyl, n-hexyl, etc.; the term "cycloalkyl" refers to a monovalent substituent consisting of a saturated hydrocarbon possessing at least one carbocyclic ring of three to eight carbon atoms, e.g. cyclopropyl, cyclobutyl, cyclopentyl, cyclohexyl, cycloheptyl, cyclooctyl, etc., having its free valence bond from a carbon of the carbocyclic ring; the term "aryl" refers to a monovalent substituent such as for example phenyl, o-tolyl, m-methoxyphenyl, etc., defined by the formula

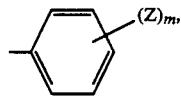

where Z and m are as defined below; the term "aralkyl" refers to a monovalent substituent which consists of an "aryl" group, e.g. phenyl, o-tolyl, m-methoxyphenyl, etc., defined by the formula

where Z is as defined below and m is an integer of 1 to 2, linked through a loweralkylene group having its free valence bond from a carbon of the loweralkylene group, and having a formula of -loweralkylene

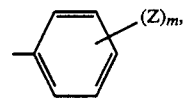

where Z is hydrogen, halogen, loweralkyl, and loweralkoxy, the term "alkylene" refers to a bivalent radical of the lower branched or unbranched alkyl group it is derived from having valence bonds from two terminal carbons thereof, e.g. ethylene (—CH$_2$CH$_2$—), propylene (—CH$_2$CH$_2$CH$_2$—), isopropylene

etc.; and the term "halogen" refers to a member of the halogen family consisting of fluorine, chlorine, bromine and iodine.

The compounds of the present invention are prepared in the following manner. The substituents R, X, Z and the integer m are as defined above unless indicated otherwise.

Eseroline of the formula,

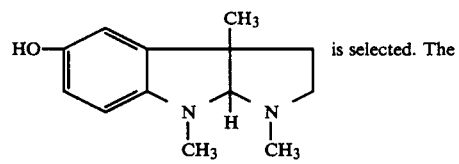 is selected. The eseroline is reacted with a carbonate (II), having the formula

 (II)

where R$_1$ is lower alkyl, cycloalkyl, aryl and aralkyl. Such compounds are all known or can be easily prepared using conventional techniques well known in the art, such as those described in "Carbonic and Chloroformic Esters" in Kirk-Othmer Encyclopedia of Chemical Technology (ECT), 3rd ed., Vol. 4, pp. 758–771, by E. Abrams. The reaction of eseroline and carbonate II is carried out under conventional reaction conditions, typically in an inert solvent, e.g. tetrahydrofuran, chloroform, dichloromethane, etc., at a temperature of 0° to the boiling point of the solvent for 10 minutes to 24 hours to form Compound III of the invention, having the formula

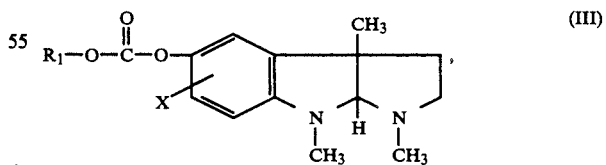 (III)

where X is hydrogen. This reaction is facilitated by the addition of a base such as sodium hydride, dimethylaminopyridine etc., prior to the addition of carbonate II.

To form Compound III of the invention where X is halogen, Compound III is reacted with an N-halosuccinimide of the formula

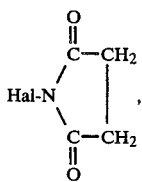

(IV)

where Hal is a halogen selected from Cl, Br and I, to form Compound III, where X is Hal. Typically the reaction is carried out in an inert solvent, e.g. dichloromethane, dimethylformamide, etc., at a temperature of 0° to 50° C. for 0.5 to 24 hours.

In another embodiment, eseroline is reacted with 1,1'-carbonyldiimidazole,

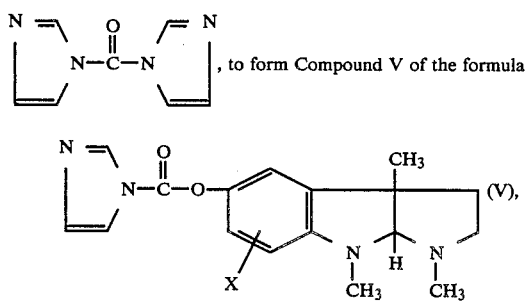

where X is hydrogen. This reaction is typically carried out in an inert solvent, e.g. tetrahydrofuran, chloroform, dichloromethane, etc. at a temperature of 0° C. to the boiling point of the solvent for 0.5 to 24 hours. Compound V in situ is in turn reacted again with equal molar quantities of eseroline, under the same reaction conditions, to form Compound VI of the invention

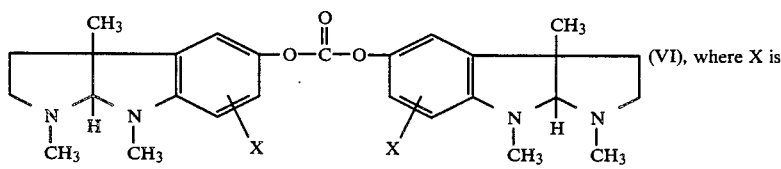

To form Compound VI of the invention where X is other than hydrogen, the procedures as described above are carried out.

Examples of some of the compounds of the invention include:

(3aS-cis)-1,2,3,3a,8,8a-hexahydro-1,3a,8-trimethylpyrrolo[2,3-b]indol-5-yl 2-methylphenyl carbonate;

(3aS-cis)-1,2,3,3a,8,8a-hexahydro-1,3a,8-trimethylpyrrolo[2,3-b]indol-5-yl 3-methylphenyl carbonate;

(3aS-cis)-1,2,3,3a,8,8a-hexahydro-1,3a,8-trimethylpyrrolo[2,3-b]indol-5-yl methyl carbonate;

heptyl (3aS-cis)-1,2,3,3a,8,8a-hexahydro-1,3a,8-trimethylpyrrolo[2,3-b]indol-5-yl carbonate;

benzyl (3aS-cis)-1,2,3,3a,8,8a-hexahydro-1,3a,8-trimethylpyrrolo[2,3-b]indol-5-yl carbonate;

cyclohexyl (3aS-cis)-1,2,3,3a,8,8a-hexahydro-1,3a,8-trimethylpyrrolo[2,3-b]indol-5-yl carbonate;

benzyl (3aS-cis)-7-bromo-1,2,3,3a,8,8a-hexahydro-1,3a,8-trimethylpyrrolo[2,3-b]indol-5-yl carbonate;

(3aS-cis)-1,2,3,3a,8,8a-hexahydro-1,3a,8-trimethylpyrrolo[2,3-b]indol-5-yl (1-phenylethyl) carbonate;

(3aR-cis)-7-bromo-1,2,3,3a,8,8a-hexahydro-1,3a,8-trimethylpyrrolo[2,3-b]indol-5-yl t-butyl carbonate;

7-bromo-1,2,3,3a,8,8a-hexahydro-1,3a,8-trimethylpyrrolo[2,3-b]indol-5-yl t-butyl carbonate.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 95, 729 (1957)]. The analgesic activity of some of the compounds expressed in terms of the $ED_{50}$ values for inhibition of writhing are given in TABLE I.

| Compound | Inhibition of Writhing $ED_{50}$ (mg/kg) |
|---|---|
| 4-chlorophenyl (3aS-cis)-1,2,3,3a,8,8a-hexahydro-1,3a,8-trimethylpyrrolo[2,3-b]indol-5-yl carbonate fumarate | 0.74 (subcutaneous) |
| (3aS-cis)-7-bromo-1,2,3,3a,8,8a-hexahydro-1,3a,8-trimethylpyrrolo[2,3-b]indol-5-yl t-butyl carbonate, sesquifumarate | 0.16 (subcutaneous) 0.40 (oral) |
| eseroline salicylate (standard) | 0.52 (subcutaneous) |

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 1% of the carbonate derivatives of eseroline of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the carbonate derivates of eseroline of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the carbonate derivatives of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the carbonate derivatives of the invention.

The solutions or suspensions may also include the following adjuvants: a sterile diluent such as water for injection, saline solution, fixed oils, polyethylene glycols, glycerine, propylene glycol or other synthetic solutions; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

4-Chlorophenyl (3aS-cis)-1,2,3,3a,8,8a-hexahydro-1,3a,8-trimethylpyrrolo [2,3-b]indol-5-yl carbonate fumarate A degassed solution of eseroline (4 g, 18.3 mmol) in 250 ml tetrahydrofuran (THF) was treated in one portion with NaH (1.1 eq., 0.97 g of a 50% dispersion in oil) and stirred at room temperature for 20 minutes. Bis(4-chlorophenyl)carbonate (2.5 eq., 13.03 g) was added and the mixture was refluxed overnight. The reaction was cooled to room temperature and 2 ml of 95% ethanol was added. The mixture was stirred for 5 minutes and then filtered and evaporated to an oil. This residue was chromatographed (eluent: 2% methanol/dichloromethane) to yield 3.4 g (49.8%) of a purified oil. The fumarate was prepared by combining a solution of the oil in methanol with 1 equivalent of fumaric acid dissolved in methanol, and then adding ether followed by pentane to induce crystallization of the product salt. This afforded 1.7 g of pure 4-chlorophenyl (3aS-cis)-1,2,3,3a,8,8a-hexahydro-1,3a,8-trimethylpyrrolo[2,3-b]indol-5-yl carbonate fumarate, m.p. 91°–93° C.

Analysis: Calculated for $C_{20}H_{21}ClN_2O_3 \cdot C_4H_4O_4$: 58.95% C 5.16% H 5.73% N. Found: 58.66% C 5.27% H 5.84% N.

EXAMPLE 2 t-Butyl (3aS-cis)-1,2,3,3a,8,8a-hexahydro-1,3a,8-trimethylpyrrolo [2,3-b]indol-5-yl carbonate fumarate hemihydrate To a degassed solution of eseroline (4.61 g, 21.2 mmoles) in 75 ml of chloroform at 0° C. was added dimethylaminopyridine (DMAP; 2.6 g, 1.0 eq.) and a solution of di-t-butylcarbonate (7.8 g, 1.5 eq.) in 10 ml of chloroform. After 10 minutes at 0° C., the solvent was evaporated and the residue was extracted into hexane and the insolubles were filtered off. The crude oil from hexane was purified by flash chromatography (60 g of $SiO_2$, eluted with 0.5% of $CH_3OH$ in dichloromethane: 2 l) to give a purified oil (6 g, 90%). A 1.45 g portion of the oil was dissolved into ether and treated with a solution of fumaric acid (528 mg, 1.0 eq.) in ethanol. The solvent was removed to dryness. The material left was recrystallized twice from ethanol-isopropyl ether (5:15 ml) and acetone:isopropyl ether (4:4 ml) to yield t-butyl (3aS-cis)-1,2,3,3a,8,8a,-hexahydro-1,3a,8-trimethylpyrrolo [2,3-b]indol-5-yl carbonate fumarate hemihydrate: 587 mg, m.p. 132°–133° C.

Analysis: Calculated for $C_{18}H_{26}N_2O_3 \cdot C_4H_4O_4 \cdot 0.5 H_2O$: 59.58% C 7.05% H 6.32% N. Found: 59.89% C 6.84% H 6.28% N.

EXAMPLE 3

(3aS-cis)-7-Bromo-1,2,3,3a,8,8a-hexahydro-1,3a,8-trimethylpyrrolo[2,3-b]indol-5-yl t-butyl carbonate sesquifumarate To a degassed solution of the t-butylcarbonate of eseroline of Example 2 (2.56 g, 8.05 mmoles) in 10 ml of dichloromethane was added a solution of N-bromosuccinimide (1.53 g, 1.05 eq.) in dichloromethane (25 ml). After 30 minutes at room temperature the solvent was evaporated and the residue was purified by flash chromatography (35 g of $SiO_2$, eluted with dichloromethane: 1 l) to give a purified oil (2.9 g, 90%). This oil was dissolved into ether and treated with a solution of fumaric acid in ethanol (850 mg, 1.0 eq.). The solvent was concentrated to dryness. The residue was dissolved into acetone and filtered once, then was concentrated down to about 7 ml when isopropyl ether was added slowly to allow crystallization. The crystals, which formed shortly, were collected and dried to yield 2.16 g of (3aS-cis)-7-bromo-1,2,3,3a,8,8a-hexahydro-1,3a,8-trimethylpyrrolo[2,3-b]indol-5-yl t-butyl carbonate sesquifumarate, m.p. 146°–147.5° C.

Analysis: Calculated for $C_{18}H_{25}BrN_2O_3 \cdot 1.5C_4H_4O_4$: 50.44% C 5.47% H 4.90% N. Found: 50.59% C 5.34% H 4.86% N.

EXAMPLE 4 bis(3aS-cis)-1,2,3,3a,8,8a-hexahydro-1,3a,8-trimethylpyrrolo[2,3-b]indol-5-yl carbonate A degassed solution of eseroline (2 g, 9.2 mmol) in 50 ml of dichloromethane was treated in one portion with 1,1'-carbonyldiimidazole (1.5 g, 1 eq.) then stirred at room temperature for 1 hour. Another equivalent of eseroline (2 g, 9.2 mmol) was added to the solution and the reaction mixture stirred overnight at room temperature under nitrogen. The solution was concentrated to a residue and purified by alumina chromatography (50% ethyl acetate/dichloromethane) followed by silica gel flash chromatography (15% methanol/acetone) to yield an oil (1.15 g, pure by thin layer chromatography). This oil was crystallized from hot petroleum ether to give 0.7 g of bis(3aS-cis)-1,2,3,3a,8,8a-hexahydro-1,3a,8-trimethylpyrrolo[2,3-b]indol-5-yl carbonate, m.p. 101°–102° C.

Analysis: Calculated for $C_{27}H_{34}N_4O_3$: 70.09% C 7.42% H 12.11% N. Found: 70.05% C 7.39% H 12.20% N.

We claim:

1. A carbonate derivative of eseroline of the formula

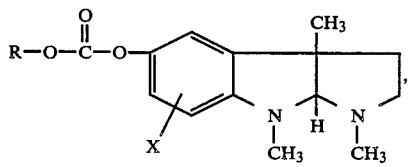

where R is lower alkyl, cycloalkyl, aryl, aralkyl and

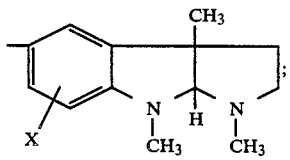

X is hydrogen and halogen; the pharmaceutically acceptable acid addition salts thereof and where applicable the optical isomers and racemic mixtures thereof.

2. The compound as defined in claim 1 which is 4-chlorophenyl (3aS-cis)-1,2,3,3a,8,8a-hexahydro-1,3a,8-trimethylpyrrolo [2,3-b]indol-5-yl carbonate and the pharmaceutically acceptable addition salts thereof.

3. The compound as defined in claim 2 wherein said salt is the fumarate.

4. The compound as defined in claim 1 which is t-butyl (3aS-cis)-1,2,3,3a,8,8a-hexahydro-1,3a,8-trimethylpyrrolo[2,3-b]indol-5-yl carbonate and the pharmaceutically acceptable addition salts thereof.

5. The compound which is t-butyl (3a5-cis)-1,2,3,3a,8-,8a-hexahydro-1,3a,8-trimethylpyrrolo[2,3-b]indol-5-yl carbonate fumarate hemihydrate.

6. The compound as defined in claim 1 which is (3aS-cis)-7-bromo-1,2,3,3a,8,8a-hexahydro-1,3a,8-trimethylpyrrolo[2,3-b]indol-5-yl t-butyl carbonate and the pharmaceutically acceptable addition salts thereof.

7. The compound as defined in claim 6 wherein said salt is the sesquifumarate.

8. The compound as defined in claim 1 which is bis(-3aS-cis)-1,2,3,3a,8,8a-hexahydro-1,3a,8-trimethylpyrrolo[2,3-b]indol-5-yl carbonate and the pharmaceutically acceptable addition salts thereof.

9. An analgesic composition which comprises an effective pain alleviating amount of a compound of the formula

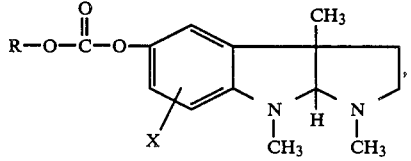

where R is lower alkyl, cycloalkyl, aryl, aralkyl and

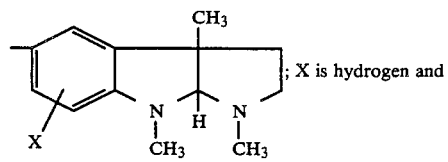

; X is hydrogen and halogen; the pharmaceutically acceptable acid addition salts thereof and where applicable the optical isomers and racemic mixtures thereof; and a suitable carrier therefor.

10. The composition as defined in claim 9 which comprises 4-chlorophenyl (3aS-cis)-1,2,3,3a,8,8a-hexahydro-1,3a,8-trimethylpyrrolo [2,3-b]indol-5-yl carbonate and the pharmaceutically acceptable addition salts thereof.

11. The composition as defined in claim 10 wherein said salt is the fumarate.

12. The composition as defined in claim 9 which comprises t-butyl (3aS-cis)-1,2,3,3a,8,8a-hexahydro-1,3a,8-trimethylpyrrolo[2,3-b]indol-5-yl carbonate and the pharmaceutically acceptable addition salts thereof.

13. An analgesic composition which comprises an effective pain alleviating amount of t-butyl (3a5-cis)-1,2,3,3a,8,8a-hexahydro-1,3a,8-trimethylpyrrolo[2,3-b]indol-5-yl carbonate fumarate hemihydrate.

14. The composition as defined in claim 9 which comprises (3aS-cis)-7-bromo-1,2,3,3a,8,8a-hexahydro-1,3a,8-trimethylpyrrolo[2,3-b]indol-5-yl t-butyl carbonate and the pharmaceutically acceptable addition salts thereof.

15. The composition as defined in claim 14 wherein said salt is the sesquifumarate.

16. The composition as defined in claim 9 which comprises bis(3aS-cis)-1,2,3,3a,8,8a-hexahydro-1,3a,8-trimethylpyrrolo[2,3-b]indol-5-yl carbonate and the pharmaceutically acceptable addition salts thereof.

17. A method of alleviating pain in a mammal which comprises administering to a mammal a pain alleviating effective amount of a compound of the formula

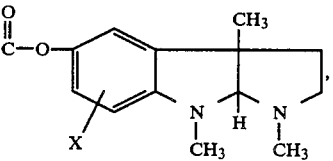

where R is lower alkyl, cycloalkyl, aryl, aralkyl and

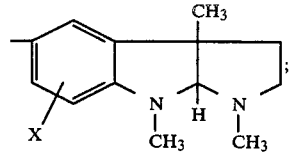

-continued

X is hydrogen and halogen; the pharmaceutically acceptable acid addition salts thereof and where applicable the optical isomers and racemic mixtures thereof.

18. The method as defined in claim 17 wherein said compound is 4-chlorophenyl (3aS-cis)-1,2,3,3a,8,8a-hexahydro-1,3a,8-trimethylpyrrolo[2,3-b]indol-5-yl carbonate and the pharmaceutically acceptable addition salts thereof.

19. The method as defined in claim 18 wherein said salt is the fumarate.

20. The method as defined in claim 17 wherein said compound is t-butyl (3aS-cis)-1,2,3,3a,8,8a-hexahydro-1,3a,8-trimethylpyrrolo[2,3-b]indol-5-yl carbonate and the pharmaceutically acceptable addition salts thereof.

21. A method of alleviating pain in a mammal which comprises administering to a mammal a pain alleviating amount of t-butyl(3aS-cis)-1,2,3,3a,8,8a-hexahydro-1,3a,8-trimethylpyrrolo[2,3-b]-indol-5-yl carbonate fumarate hemihydrate.

22. The method as defined in claim 17 wherein said compound is (3aS-cis)-7-bromo-1,2,3,3a,8,8a-hexahydro-1,3a,8-trimethylpyrrolo[2,3-b]indol-5-yl t-butyl carbonate and the pharmaceutically acceptable addition salts thereof.

23. The method as defined in claim 22 wherein said salt is the sesquifumarate.

24. The method as defined in claim 17 wherein said compound is bis(3aS-cis)-1,2,3,3a,8,8a-hexahydro-1,3a,8-trimethylpyrrolo[2,3-b]indol-5-yl carbonate and the pharmaceutically acceptable addition salts thereof.

* * * * *